(12) United States Patent
Wong et al.

(10) Patent No.: US 7,464,606 B2
(45) Date of Patent: Dec. 16, 2008

(54) BEND TESTING APPARATUS AND METHOD OF CARRYING OUT THE SAME

(75) Inventors: Ee Hua Wong, Singapore (SG); Kah Woon Seah, Singapore (SG); Ranjan s/o Rajoo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 179 days.

(21) Appl. No.: 11/406,546

(22) Filed: Apr. 18, 2006

(65) Prior Publication Data

US 2007/0256503 A1 Nov. 8, 2007

(51) Int. Cl.
*G01N 3/32* (2006.01)
(52) U.S. Cl. .......................................... 73/812; 73/849
(58) Field of Classification Search ............ 73/766–856
See application file for complete search history.

(56) References Cited

U.S. PATENT DOCUMENTS

| | | | |
|---|---|---|---|
| 2,696,736 A | | 12/1954 | Frederick |
| 3,769,860 A | * | 11/1973 | Frings et al. .................. 81/429 |
| 4,321,834 A | | 3/1982 | Oliver ......................... 79/217 |
| 4,326,421 A | | 4/1982 | Pilesi et al. |
| 4,379,410 A | | 4/1983 | Fritts et al. ..................... 73/809 |
| 6,393,890 B1 | * | 5/2002 | Scholeck .................. 72/390.3 |

FOREIGN PATENT DOCUMENTS

| | | |
|---|---|---|
| GB | 556504 | 10/1943 |
| GB | 1352315 | 10/1943 |
| GB | 897720 | 5/1962 |
| GB | 1201832 | 8/1970 |
| GB | 2097938 | 11/1982 |

OTHER PUBLICATIONS

Yamaguchi et al., *Development of Long-term Creep-fatigue Testing Machines*, 1986, pp. 1952-1957.
Hu et al., *The Influence of Cyclic Loading on the Wear of a Dental Composite*, Biomaterials 20 (1997) 907-912.

* cited by examiner

*Primary Examiner*—Max Noori
(74) *Attorney, Agent, or Firm*—Niky Economy Syrengelas, Esq.; Crockett & Crockett

(57) ABSTRACT

A bend testing apparatus for simulating free vibrational flexing at high speeds and frequencies in a test specimen, said apparatus comprising a cam having a narrow circumferential profile or linear profile wherein at least one portion of the profile of said cam comprises at least one waveform, a specimen holder that holds the test specimen on opposite ends of the test specimen in a default position, a light-weight deformation member operable to deflect at least one point on the test specimen from the default position, a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam.

35 Claims, 12 Drawing Sheets

BEND TESTING APPARATUS AND METHOD OF CARRYING OUT THE SAME

TECHNICAL FIELD

The invention relates to the field of testing apparatus for impact testing printed circuit boards (PCB) and electronic components mounted thereon, and more particularly to a high-speed bend testing apparatus for simulating free vibrational flexing in the testing of PCBs.

BACKGROUND

In the electronic packaging industry, printed circuit board (PCB) assemblies having electrical components mounted thereon are tested against drop impact by the typical board-level drop test, whereby a board assembly is dropped from a certain height and experiences a sharp acceleration pulse upon impact. The main focus of the drop test is to assess the reliability of the interconnectors, which provide the physical and electrical connection between the PCB and the electrical components mounted thereon.

It has been found that the major failure driver in these tests is the free vibrational flexing of the PCBs after impact. It is also recognized that the drop test method is time-consuming owing to the time required to raise the board assembly to the drop height and the quantity of drops required in standard testing. The drop test method is also inconsistent owing to the high accelerations and forces causing loosening of screws and wear of mechanical fixtures. An effective solution to these problems would be a bend test which performs bending at the free vibration frequencies of PCB assemblies which range from 200 Hz to 1000 Hz at accelerations of up to 3000 g (where g is the acceleration due to gravity) taken at the midpoint of the PCB. Such a test should be able to cut testing times by a factor of at least 20 and should also be more controllable and consistent owing to the absence of the large impact forces on the fixtures. Examples of such bend testers and methods for simulating the free vibrational flexing of PCBs include electromagnetic shakers and universal static testers, for example. However, these testers do not comply with the above-mentioned frequency and acceleration requirements.

Existing equipment and methods for including bending loads are, as mentioned above, inadequate for reproducing the bending frequencies of a test specimen subjected to drop testing. The universal static test has a maximum test frequency of only several Hertz (Hz), and present electromagnetic shakers fall far short of the required 1000 Hz and 3000 g flexural vibration requirements.

Therefore, there is a need for a high-speed bend tester that is capable of simulating flexure over a wide range of frequencies at accelerations of up to several thousand g's and that is cost effective to produce and operate as well.

SUMMARY

The present invention provides a bend testing apparatus for simulating free vibrational flexing at high speeds and frequencies in a test specimen, said apparatus comprising: a cam having a circumferential profile wherein at least one portion of the profile of said cam comprises at least one waveform, a specimen holder that holds the test specimen on opposite ends of the test specimen in a default position, a deformation member operable to deflect at least one point on the test specimen from the default position. The apparatus further comprises a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam.

The present invention also provides for a bend testing apparatus for simulating free vibrational flexing at high speeds and frequencies in a test specimen, said apparatus comprising a cam having a profile wherein said profile comprises at least one waveform on at least one circumferential portion of the cam, a specimen holder that holds a test specimen on opposite ends of the test specimen in a default position, a deformation member operable to deflect at least one point on the test specimen from the default position. The apparatus further comprises a follower with one end in operable contact with the cam and its other end connected to a lever, said lever being pivotally borne by a pivot at a position between the two ends thereof, to achieve an opposite movement of the one end of the lever and the deformation member connected thereto with respect to the movement of the other end of the lever operably connected with the follower, such that the displacement of the follower is according to the profile of the cam, thereby actuating the deformation member, via the pivotally borne lever, and to deflect the at least one point on the test specimen from said default position upon movement of the cam, and an adjusting mechanism operably connected to the pivot, by which the position of the pivot can be adjusted along the axis of the lever.

The present invention further provides for a method of bend testing a test specimen at high speeds and frequencies. The method comprises:

Providing a bend testing apparatus comprising a cam having a circumferential profile wherein at least one portion of the profile of said cam comprises at least one waveform, a specimen holder that holds the test specimen on opposite ends of the test specimen in a default position, a deformation member operable to deflect at least one point on the test specimen from the default position, a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam; and Rotating the cam such that the at least one portion of the profile that comprises at least one waveform actuates the follower.

The bend testing apparatus as defined in the appended independent claims offers an efficient and accurate means of testing test specimens via the simulation of vibrational flexing and hence, their reliability when subjected to a drop impact.

The invention will be better understood with reference to the following detailed description of the invention, exemplary embodiments and drawings, in which:

DETAILED DESCRIPTION

Figure 1:
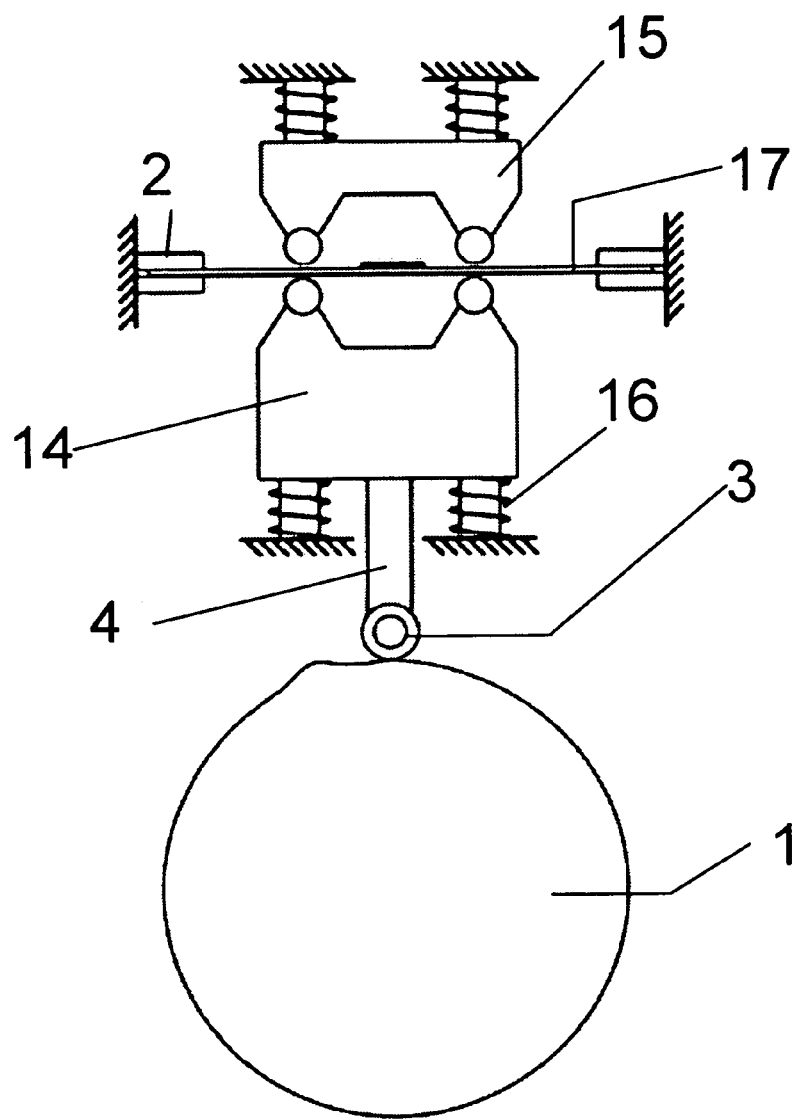
FIG. 1 shows a side view of an embodiment of a high-speed bend testing apparatus according to the invention.

A high-speed bend testing apparatus for simulating free vibrational flexing in the testing of PCBs, according to the present invention, comprises a cam having a profile wherein said profile comprises at least one waveform on at least one portion of the circumference of the cam, a specimen holder that holds a test specimen on opposite ends of the test specimen, an actuatable deformation member operable to deflect at least one point of the test specimen when said specimen is held by the specimen holder, and a follower. The follower has one end operably in contact with the cam and its other end connected to the deformation member, such that the follower follows the profile of the cam and actuates the deformation member correspondingly.

The cam is typically moveable linearly or rotationally and may be substantially circular in shape with its circumferential profile having the at least one waveform. Any waveform that is able to actuate the follower sufficiently to satisfy the requirements of bend testing may be used. For example, the at least one waveform may be a crest, a trough or a sinusoid, for example. Using the example of a sinusoid, in one illustrative embodiment, the sinusoid feature is at the circumferential portion of the cam. In another embodiment of the cam, a second circumferential portion of the cam having the sinusoid may be diametrically opposite the first sinusoid feature.

In the embodiment having two sinusoidal features diametrically opposite each other, the frequency at which the sinusoidal feature is applied to the deformation member via the follower is doubled. Accordingly, the profile may also have a plurality (two or more) of sinusoidal features. In this embodiment the sinusoidal features are arranged along the circumference of the cam in a circumferentially equidistant manner.

As a further illustrative example, another embodiment of the cam may have three sinusoidal features along its circumference. In this illustrative example, the three sinusoidal features are arranged such that the angle between each sinusoidal feature, when taken about the circumference of the cam, is about 120 degrees. Similarly, should the cam have four sinusoidal features along its circumference, the angle between each sinusoidal feature, when taken about the circumference of the cam, is about 90 degrees.

The follower, as mentioned above, is operably connected to the cam. As an illustration, in one embodiment, the follower may be considered to be a rigid body having a wheel at one end that follows the profile of the cam as the cam rotates about its axis of rotation. An alternative manner in which the follower may be operably connected to the cam may be to provide a cam with a groove along the circumference of said cam. Within the groove, the profile of the cam is contained and the follower being guided by said groove and follows the profile of the cam accordingly.

Accordingly, the follower oscillates itself vertically in relation to the frequency at which the cam rotates. As the other end of the follower is attached to the deformation member, the deformation member exerts a force on the specimen also in relation to the frequency at which the follower (and therefore the cam) oscillates.

The testing apparatus may further comprise a motor. In one embodiment, the motor is adapted to rotate the cam about an axis of rotation. In another embodiment of the invention, the motor may be adapted to translate the cam linearly. The embodiment having a rotatable cam further comprises a clutch adapted to engage said cam at its axis of rotation at a suitable motor speed. The motor speed is typically between the ranges of about 500-about 2000 rpm, but is not limited thereto.

The clutch adapted to engage the cam along its axis of rotation is adapted to have a fast response time. In one exemplary embodiment, a suitable response time of the clutch, in order to generate a single pulse load to the test specimen, is considered to be less than about 30 milliseconds (ms). This is because given a benchmark motor speed of about 2000 rpm (i.e. it takes about 30 milliseconds (ms) for the motor to make one revolution), the clutch engagement will have to occur within a period of one revolution, or within about 30 ms. In a further exemplary embodiment, where the response time is about 60 ms, the motor speed is about 1000 rpm. Examples of clutches that have such suitable response times include, but are not limited to a wafer magnetic clutch or a magnetic particle clutch or a reduced-armature-gap clutch.

In another embodiment, the high-speed testing apparatus comprises a flywheel arranged between the motor and the clutch. In such an embodiment the use of an "over-excitation" method of clutch engagement achieves a rapid engagement of the clutch to the cam. Over-excitation involves applying a sharp electrical pulse of about 5 to 8 times the normal operating voltage for a very short time at the start of engagement. The voltage is then rapidly reduced to normal levels to avoid damage to the clutch.

In embodiments where the cam is rotatable, the cam is typically in the form of a disc. The disc may be advantageously made to have a low inertial mass so as to facilitate the engagement of the clutch. In this regard, it may be suitable for the cam to be essentially circular while having a profile detailed with various waveforms to simulate the required bending effects on the test specimen. The cam may be fabricated from any suitable material that satisfies the requirements of the cam having a low inertia. Examples of such materials may be fiber-reinforced composites, carbon fiber, polycarbonate, titanium or aluminum.

In a further embodiment of the invention, the high-speed bend tester, according to the present invention, further comprises a pivot, which bears a lever in a pivotal manner at a position between the two ends of said lever. In this embodiment, one end of the lever is connected to the deformation member, with the other end connected to the follower. The effect of the lever being pivotally borne in this manner results in an opposite movement of the one end of the lever, and the deformation member connected thereto, with respect to the movement of the other end of the lever. This lever moves according to the operating movement of the follower, which contacts the cam. The pivotal point includes an adjusting mechanism connected to the pivot. Accordingly the position of the pivot itself can be adjusted along the axis of the lever. The adjusting mechanism may be controlled by a motor or even adjusted by manually. In order to have a high degree of precision, an exemplary embodiment of the present invention having said motor controlled adjusting mechanism may have the motor controlled by a computer program element.

In one embodiment, the linear translation of the deformation member is converted to an angular rotation. This is achieved where the specimen holder is a bearing-mounted specimen holder that is rotatable and hence, is capable of converting said linear deflection of the test specimen into an angular rotation. Owing to the rotational nature of the load, the torsional stiffness of the specimen holders may be adjusted to easily achieve both twisting and bending of the specimen.

In a further embodiment, the apparatus may include a displacement transducer. The displacement transducer includes a push rod slidably mounted within a housing. A free end of the push rod (i.e. an end outside the housing) is connected to the deformation member and the housing is fixed to a rigid reference frame. The rigid reference frame may be located either upon the apparatus or may be based on a further reference point. In this arrangement, a bending displacement of the test specimen results in a sliding displacement of the push rod with respect to the fixed housing. Accordingly, when the cam generates a displacement of the test specimen, and as amplified by the lever, said displacement is directly measurable and verifiable via said displacement transducer. Examples of suitable displacement transducers include, but are not limited to, linear variable displacement transducers (LVDT) and Half-bridge transducers with fast response times.

In another embodiment, the apparatus includes specimen holders rigidly supported on load transducers. The load transducers rigidly supported and bolted to the specimen holders such that when a force applied to the test specimen via the deformation member, said force is measurable by said load transducers. In this embodiment, when a force is applied to the test specimen during testing, said force is measurable. Examples of load transducers with fast response include, but are not limited to, piezoelectric, strain-gauge, capacitive and piezoresistive load cells.

In a further embodiment, the apparatus may further include a compact temperature chamber which encloses the specimen and allows testing to be conducted at low temperatures. The chamber walls contain openings for the deformation members and PCB to pass through. Examples of materials used for the compact temperature chamber include, but are not limited to, rockwool, rubber foam and Styrofoam insulation panels. Examples of cooling methods include, but are not limited to, liquid nitrogen cooling and thermoelectric cooling.

With regard to one embodiment of the invention, a method for bend testing a test specimen includes Providing a bend testing apparatus comprising a cam having a circumferential profile wherein at least one portion of the profile of said cam comprises at least one waveform, a specimen holder that holds the test specimen on opposite ends of the test specimen in a default position, a deformation member operable to deflect at least one point on the test specimen from the default position, follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam; and Moving the cam such that the at least one portion of the profile that comprises at least one waveform actuates the follower.

A further method of bend testing a test specimen using another embodiment of the invention includes Providing a bend testing apparatus comprising:
 a cam having a profile wherein said profile comprises at least one waveform on at least one circumferential portion of the cam,
 a specimen holder that holds a test specimen on opposite ends of the test specimen in a default position,
 a deformation member operable to deflect at least one point on the test specimen from the default position,
 a follower with one end in operable contact with the cam and its other end connected to an end of a lever, said lever being pivotally borne by a pivot at a position between the two ends thereof, to achieve an opposite movement of the one end of the lever and the deformation member connected thereto with respect to the movement of the other end of the lever operably connected with the follower, such that the displacement of the follower is according to the profile of the cam, thereby actuating the deformation member, via the pivotally borne lever, and to deflect the at least one point on the test specimen from said default position upon movement of the cam, and
 an adjusting mechanism operably connected to the pivot, by which the position of the pivot can be adjusted along the axis of the lever; and Moving the cam such that the at least one portion of the profile that comprises at least one waveform actuates the follower.

With regard to the above-mentioned method of carrying out bend testing, the flexing frequency of the test samples is determined by the motor rpm and the circumferential angle on the cam profile over which the waveform is spread. Examples of testing methods to conduct bend testing of samples are now described.

One exemplary method of testing test samples may involve the continuous running of the motor and thereby the cam connected thereto. This will result in the specimen being deflected at intervals which depend on the motor rpm and the number of waveforms on the cam profile. As an illustrative example, if there are two waveforms on the cam profile spaced apart at 180° (i.e. at diametrically opposite ends), and the motor is running at 600 rpm, the specimen will be deflected at intervals of 0.05 seconds.

The frequency of each deflection is a function of motor speed and waveform angle. Again, for illustrative purposes, and according to the relationship of $f=2\pi/\theta(\omega)$, where $f$ is the test frequency, $\theta$ is the rise angle (in radian) and $\omega$ is the motor speed (revolutions per second) assuming that the waveform of the cam profile is sinusoidal having a waveform angle of about 24° (about 0.4188 rad), while the motor runs at a speed of about 600 rpm (or 10 revolutions per second), the frequency of the sinusoid deflection pulse will be about 150 Hz.

Alternatively, during the continuous bend testing method as described above, the specimen may be subjected to a series of deflections at various amplitudes and/or frequencies. The amplitude may be adjusted by moving the location of the pivot along said lever, while the frequency may be adjusted by changing the speed at which the motor rotates, i.e. a higher or lower rpm. As a further alternative, a complex series of deflections may be handled by computer programming which automatically adjusts the location of the pivot and the rpm.

Another exemplary method of carrying out bend testing is to subject the test sample to a discrete number of deflections. In such discrete testing, the deflections of the test specimen may be stopped immediately in cases where a change in the deflection amount or deflection frequency is desired within a series of varying deflection amplitudes and frequencies. In this regard, the test apparatus may further include a braking mechanism that would enable the cam to be brought to a halt after a given number of discrete deflections or after even a single deflection.

In all the above-mentioned exemplary testing methods, the cam may be required to stop rotating should the specimen fail during testing. Should the test sample fail during testing, it would be crucial to prevent further damage to the specimen and to retain the initial failure condition of the test specimen for failure analysis. Accordingly, the bending deflections (rotation of the cam) may be stopped by either disengaging the clutch followed by a braking of the cam shaft.

With regard to the above-mentioned bend testing methods, possible test specimens include, but are not limited to, PCBs and substrates, for example. Accordingly, the bend tester according to the present invention may also be used to test the flexural properties of other materials.

DETAILED DESCRIPTION OF EXEMPLARY EMBODIMENTS

FIG. 1 shows a side view of a high-speed bend testing apparatus according to one embodiment of the invention. The apparatus includes a specimen holder 2, deformation members 14 and 15, a follower 3, a cam 1 and a motor (not shown) for rotating the cam 1. The specimen holder 2 clamps the specimen 17, which is typically a PCB, at either end as shown in the figure. The deformation members 14, 15 are positioned to be in contact with the specimen 17 as shown. At this juncture, the deformation members 14, 15 do not cause the specimen 17 to flex. The deformation members 14, 15 are mounted on springs 16 to ensure that they are in constant contact with the specimen 17. The lower deformation member 14 is connected to the follower 3, via a connecting member 4. The connecting member 4 is merely a rigid body having the follower 3, which may be a free wheel or bearing, for example, at one end and a connection to the lower deformation member 14 at the other. The follower 3 is in contact with the cam 1. The cam 1 is essentially a disc having a waveform along one portion of its circumference. The waveform may be a crest, a trough or a combination of both thereby defining a waveform such as a sinusoid, for example.

As the cam 1 rotates, the follower 3 will oscillate as it follows the cam profile. In this regard, an upward vertical displacement takes place each time the follower 3 passes over the rise of the cam 1. In turn, the lower deformation member 14 will also be raised vertically along with the follower 3. As the specimen 17 is securely clamped by the specimen holder 2, the upward movement of the deformation member 14 causes the specimen 17 to flex upwards, or in a concave manner. Conversely, when the follower passes over a drop in the profile, the specimen will flex downwards, or in a convex manner.

Figure 2:
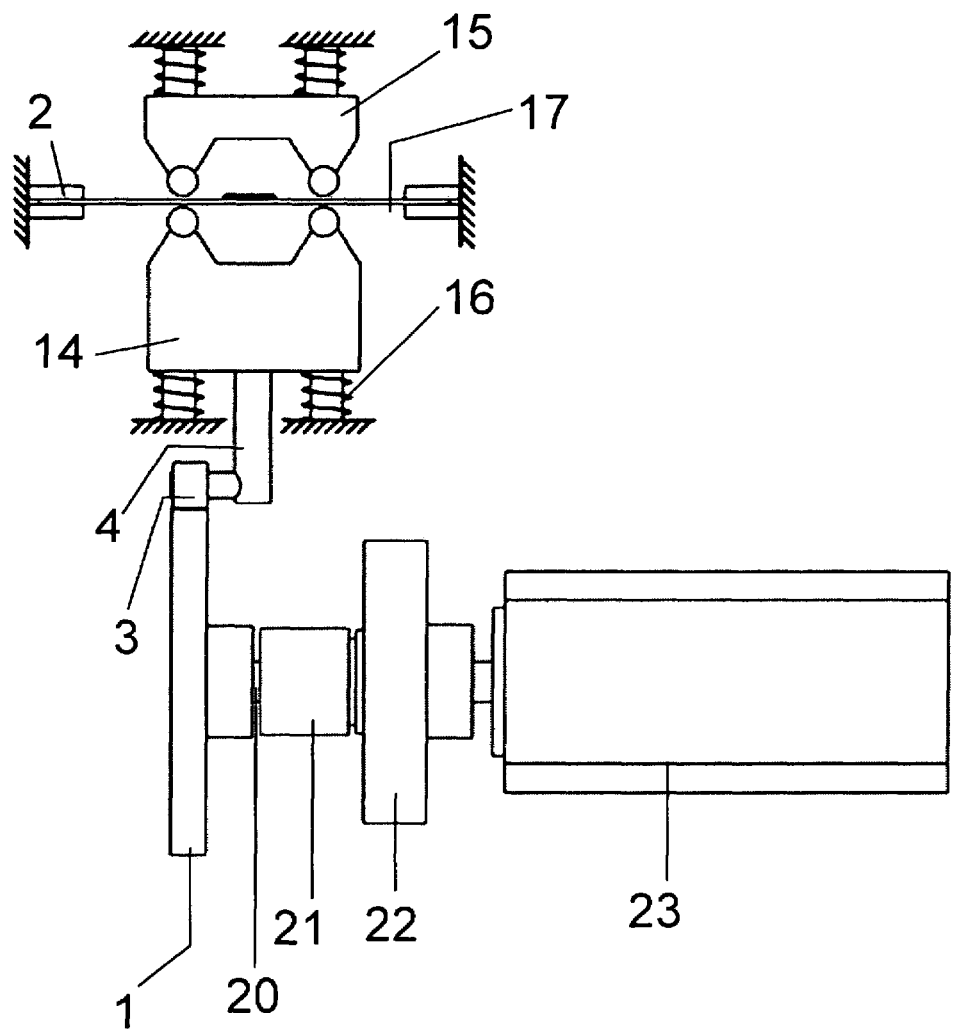
FIG. 2 shows another side view of the embodiment of the bend testing apparatus of FIG. 1.

FIG. 2 shows another side view of the high-speed bend testing apparatus of FIG. 1. The specimen 17 is clamped at either end thereof by the specimen holder 2. The specimen 17 is also contacted on either of its lateral surfaces by the lower and upper deformation members 14 and 15 respectively. The deformation members are mounted on springs, which press the deformation members 14, 15 onto the respective lateral surfaces of the specimen 17. The springs 16 enable the deformation members 14, 15 to maintain constant contact with the specimen 17 without deflecting the specimen 17. The lower deformation member 14 is connected to a connecting member 4, which has a follower 3 at its corresponding end. The follower 3 is in operable contact with the cam 1. In this regard, the follower 3 contacts the circumferential thickness of the cam 1. The cam 1 is typically left disengaged when not in use. The present apparatus also includes a motor 23 connected to a fast response clutch 21 and to a flywheel 22. The motor 23, which is directly connected to the flywheel 22, spins the fly wheel to the desired speed whereupon the clutch 21, which is also attached to the flywheel 22, is engaged. When engaged, the clutch drives a shaft 20, which is connected to the cam 1. The rapid engagement of the cam 1 via the shaft 20, by the clutch 21, through use of the flywheel 22, allows uniform deflections of the specimen 17 because the motor 23 is allowed to achieve a stable (or desired) speed before the deflections on the specimen 17 are applied.

Figure 3:
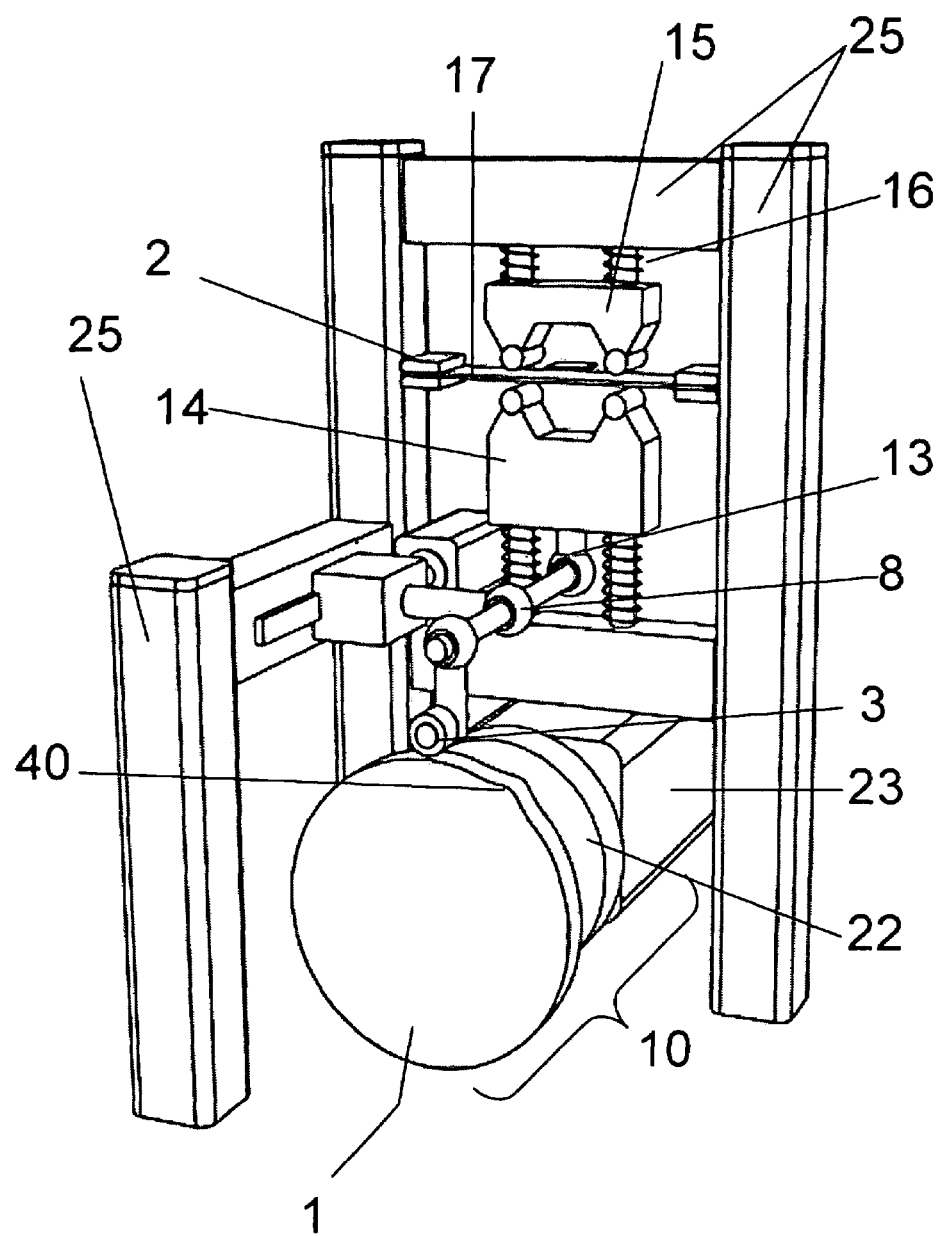
FIG. 3 shows an isometric view of another embodiment of a bend tester according to the present invention.

FIG. 3 shows a perspective view of another embodiment of the high-speed bend testing apparatus according to the invention. The apparatus includes a specimen holder 2, a specimen 17 clamped at either end thereof by the specimen holder 2, deformation members 14 and 15, an apparatus frame 25 and a cam assembly 10.

The deformation members 14 and 15 are the lower deformation member 14 and the upper deformation member 15 respectively. The deformation members 14 and 15 are mounted on compression springs 16. The upper deformation members are supported by the apparatus frame 25 and with the compression springs 16, the upper deformation member 15 is bias downwards to contact the specimen 17. The deformation member may be adapted to provide suitable contact points along the specimen 17 to provide for single or multiple point bending. For example, the contact points of the deformation members 14, 15 on the specimen 17 may be in the form of cylindrical bodies which contact the lateral surface of the specimen 17 on either side of the electrical component.

The cam assembly 10 comprises a cam 1, a fast response clutch (not shown), a flywheel 22, a motor 23, a shaft 20, and a follower 3. In this embodiment of the invention, the follower 3 is linked to the lower deformation member 14 via an adjustment mechanism. The adjustment mechanism includes series of intermediate parts, which will be discussed in greater detail in FIG. 4 that follows.

The cam 1 has a profile that includes a waveform 40 that may be formed by a crest, a trough or a combination of both to give rise to a sinusoid profile. The cam profile is formed to generate, for example, a sinusoidal wave at a specific circumferential part of the otherwise circular cam disc 1. The motor 23 drives the cam disc 1. The motor 23 may either drive the cam disc 1 directly or indirectly. Should the motor 23 drive the cam disc 1 directly, consistent deflection pulses may not be possible as the motor 23 would require sufficient time spanning over several deflection pulses to attain the desired speed. However, as described above, should a fast response clutch 21 be used in conjunction with the flywheel 22, as in the previous embodiment described in FIG. 2, consistent deflection pulses would be possible.

Whether the motor 23 drives the cam disc 1 directly or indirectly, the movement of the cam disk 1 is transmitted to the lower deformation member 14 via the follower 3 and the adjustment mechanism, which will be described later in detail. The result of said movement of the cam 1 exerts a load onto the test specimen 17, via the vertical displacement of the follower 3 and the adjustment mechanism. When this happens, the lower deformation member 14, in cooperation with the upper deformation member 15, exerts a force on the specimen 17. The vertical displacement of the follower 3 corresponds to the movement/circumferential structure of the cam disk 1. When the follower 3 moves over the cam profile, which is a crest, the follower 3 is moved in an upward direction whereby the lower deformation member 14 is actuated either directly or indirectly as the case may be, to deflect the specimen 17. Correspondingly, when the follower 3 moves over the cam profile, which is a trough, the follower 3 moves in a downward direction. Depending on whether the lower deformation member 14 is actuated directly or indirectly by said follower 3, the lower deformation member may be actuated to move in either an upward or downward manner thereby deflecting the specimen accordingly.

Figure 4:
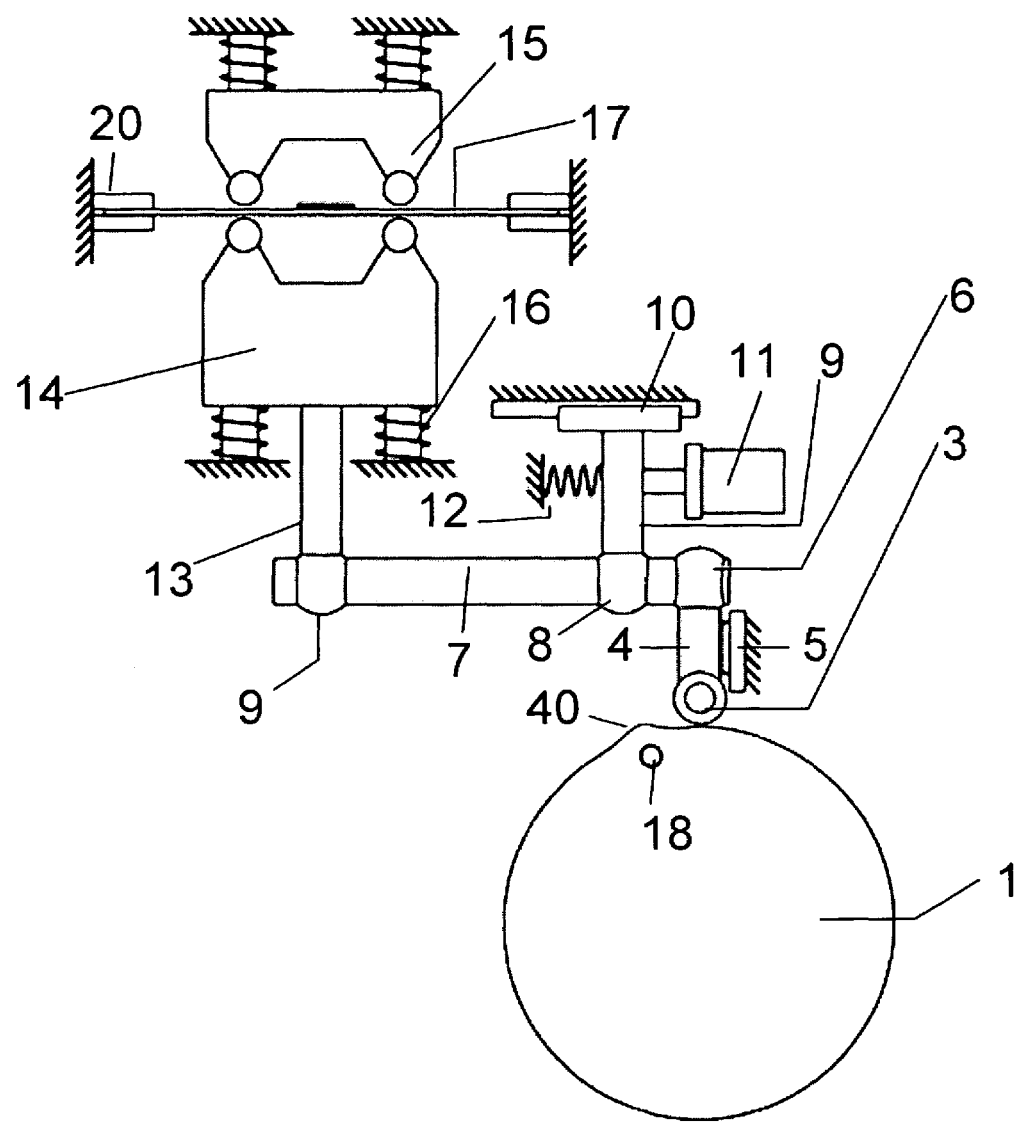
FIG. 4 shows a side view of the embodiment of the bend testing apparatus as shown in FIG. 3.

With reference to FIG. 4, the bending displacement is induced by cam 1 on which a cam follower 3 travels. The displacement waveform of the cam 1 in the present embodiment is a single bump or crest 2 over a very small angle, with the rest of the motion being a dwell. The reason for this specific cam profile is two-fold:

1) To reduce as much as possible the motor speed (rpm) required to produce a bending frequency of up to 1000 Hz. For example, a crest over an angle of 24° will reduce the rpm required by a factor of 15. Otherwise, a motor speed of 60000 rpm would be needed for a 1000 Hz test, a formidable technological challenge; and
2) To increase as much as possible the dwell time, which is the time required for the clutch and the brake to engage.

To improve the clutch engagement, the cam is designed to have a very low mass moment of inertia (I). The cam 1 shown in FIG. 4 is a solid piece. Alternatively, a spoke design may be adopted for reducing 1. The actuator driving the cam is a rotary motor 23 (see FIG. 3) that may be equipped with an encoder 24 (see FIG. 5) for measuring motor rpm.

The cam 1 motion and the displacement of the follower 3 are amplified by the adjustment mechanism mentioned previously. The adjustment mechanism includes a lever 7. The cam follower 3 is connected to an end pivot 6 of the amplifying lever 7 through a connecting member 4 which is constrained to move in only one translational direction by the linear guide 5. The middle lever pivot 8 is adjustable via a linear actuator 11 which pushes against its connecting member 9. On retraction of the linear actuator, spring 12 moves the variable pivot 8 in the opposite direction. The direction of motion is limited by the linear guide 10.

The adjustment mechanism described above aims to amplify the effect of the displacement of the follower 3. When the follower 3 is displaced vertically upwards due to following the rising portion of the crest 40 of the cam 1, the amplifying lever 7, which is pivotally mounted on pivot 8 rotates anti-clockwise about said pivot 8 such that the connecting member 9 and 13 are displaced downward. Accordingly, the lower deformation member 14 also moves downwards thereby exerting a lower pressure on the lower lateral surface of the specimen 17. In this regard, the upper deformation member 15 now exerts a greater pressure on the upper lateral surface of the specimen 17 than the pressure exerted by the lower deformation member 14 on the lower lateral surface of the specimen 17 thereby resulting in the downward concave deflection of the specimen 1.

Correspondingly, should the follower 3 be displaced vertically downwards due to its following a depression in the profile of the cam 1, the amplifying lever 7, which is pivotally mounted on pivot 8 rotates clockwise about said pivot 8 such that the connecting member 9 and 13 are displaced upward. Accordingly, the lower deformation member 14 also moves upwards thereby exerting a greater pressure on the lower lateral surface of the specimen 17. In this regard, the pressure exerted by the lower deformation member 14 on the lower lateral surface is greater than the pressure exerted by the upper deformation member 15 on the upper lateral surface of the specimen 17. This results in the upward concave deflection of the specimen 17.

Apart from amplifying the bending amplitude directed to the specimen 17, the adjustment mechanism, which includes the amplifying lever 7 and the adjustable pivot 8, also allows the bending amplitude to be adjusted automatically by software instead of manually by hand. Also, the range of adjustment may be continuous and not just at discrete increments.

It should be noted that the high accelerations encountered in high speed bend testing may necessitate the use of tough plastics such as polycarbonate (PC) or composite materials for fabricating the deformation members 14 and 15. Using metal may likely result in too high a spring stiffness being needed to prevent the specimen from losing contact with the deformation members and/or damage to the bearings.

Figure 5:
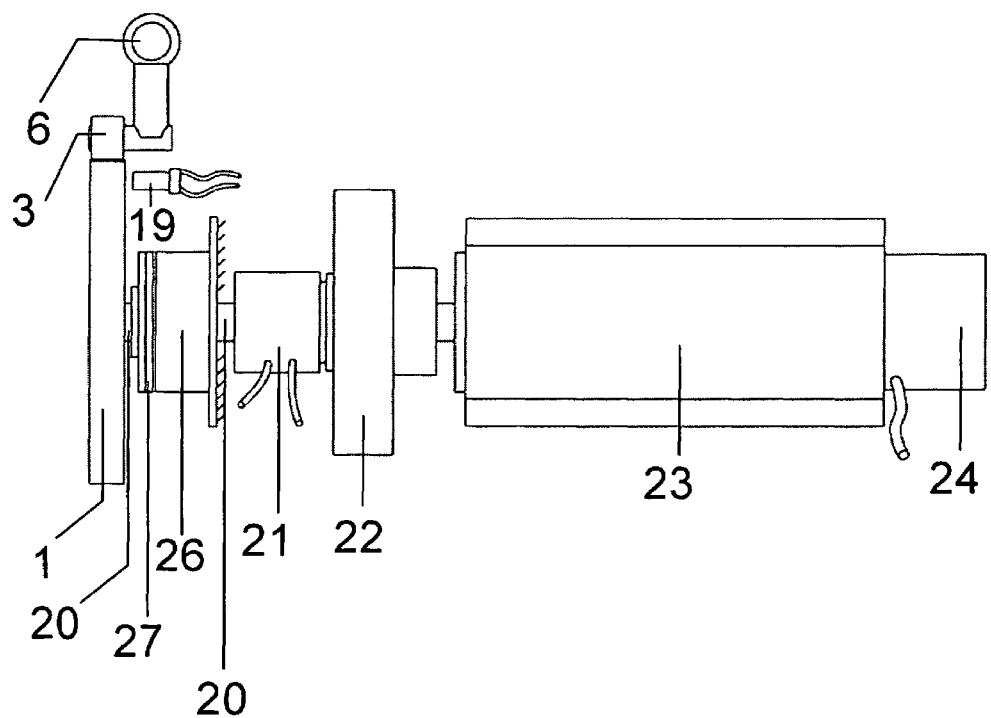
FIG. 5 shows a side view of an embodiment detailing the motor, fast response clutch and flywheel in relation to the cam.

FIG. 5 shows a side view of the embodiment of FIG. 3 and FIG. 4 detailing the shaft 20, the motor 23, fast response clutch 21, flywheel 22 and brake assembly, which comprises a coil assembly 26 and brake armature 27, in relation to the cam 1. Directly connected to the motor 23 is the flywheel 22. In this embodiment the flywheel is designed as a massive flywheel which is necessary for overcoming the extremely high torques (up to 8 Nm peak) created in this embodiment by the high speed of testing and for ensuring a smooth rotation of the cam 1. Attached to the flywheel 22 is the fast-response clutch 21. When engaged, the clutch drives the shaft 20 which is connected to the cam 1. When the clutch 21 is disengaged, shaft 20, along with the cam 1, rotates freely. Attached to the shaft 20 is the brake armature 27. When the brake coil assembly 26 is engaged, the spring loaded armature 27 is pulled and locked against the rigidly mounted brake coil assembly 26, thus bringing the shaft 20, and the cam 1 connected thereto, to a sudden stop. An essential use of the flywheel 22, brake assembly (26, 27) and fast response clutch 21 is that they allow single pulse loading of the test specimen 17 to be generated. Single pulse loading is achieved by a rapid engagement of the clutch 21 followed by a single deflection pulse, which is followed immediately by disengagement of the clutch 21 and engagement of the brake coil 26. Without the flywheel 22 and fast response clutch 21, single pulse loading at high speeds is difficult to achieve because the motor 23 needs to pick up speed and this is only done over several pulses/revolutions. Without the brake assembly (26, 27), single pulse loading is not possible because the cam 1 will only slow down after several deflection pulses.

Located on the cam 1 is a fiducial mark 18, which may take the form of an opening, or a reflective patch. A light sensor 19 detects the position of the fiducial mark 18. The light sensor 19 is also useful as it allows the rise 40 in the cam 1 to be positioned just ahead of the follower 3 at the beginning of a test, thus allowing the maximum possible dwell time for the clutch 21 to engage.

Figure 6:
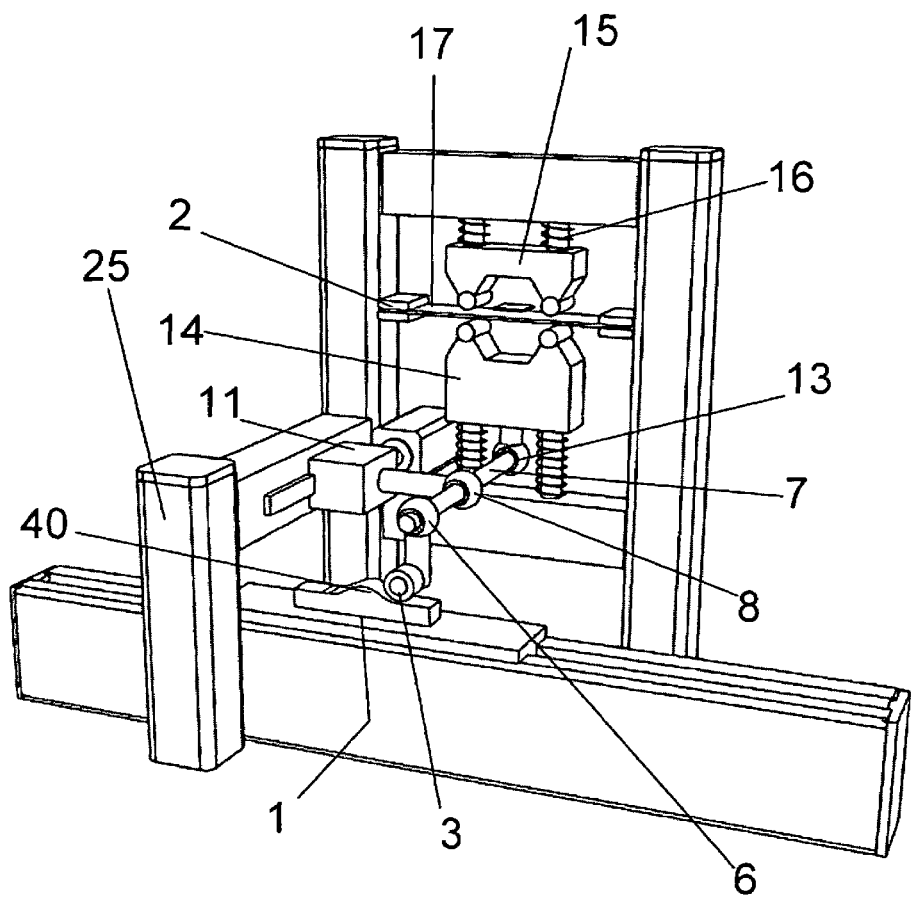
FIG. 6 shows an embodiment of the bend testing apparatus where the cam moves linearly.

FIG. 6 shows an embodiment of the bend testing apparatus where the cam moves linearly. In the embodiment of FIG. 6, the motor is adapted to move the cam 1 in a linear fashion. It is also shown in the present illustration that the cam 1 is not circular in shape but is rather elongated.

As in the embodiment shown in FIGS. 3 to 5, the motion of the cam 1 and the displacement of the follower 3 are amplified by the adjustment mechanism mentioned previously. The adjustment mechanism includes a lever 7. The cam follower 3 is connected to an end pivot 6 of the amplifying lever 7 through a connecting member 4 which is constrained to move in only one translational direction by the linear guide 5. The middle lever pivot 8 is adjustable via the linear actuator 11 which pushes against its connecting member (as in FIG. 4). On retraction of the linear actuator, spring (not shown) moves the variable pivot 8 in the opposite direction.

The adjustment mechanism described above aims to amplify the effect of the displacement of the follower 3. When the follower 3 is displaced vertically upwards due to following the rise 40 of the cam 1, the amplifying lever 7, which is pivotally mounted on pivot 8 rotates anti-clockwise about said pivot 8 such that the connecting member 9 and 13 are displaced downward. Accordingly, the lower deformation member 14 also moves downwards thereby exerting a lower pressure on the lower lateral surface of the specimen 17. In this regard, the upper deformation member 15 now exerts a greater pressure on the upper lateral surface of the specimen 17 than the pressure exerted by the lower deformation member 14 on the lower lateral surface of the specimen 17 thereby resulting in the downward concave deflection of the specimen 1.

Correspondingly, should the follower 3 be displaced vertically downwards due to its following a depression in the profile of the cam 1, the amplifying lever 7, which is pivotally mounted on pivot 8 rotates clockwise about said pivot 8 such that the connecting member 9 and 13 are displaced upward. Accordingly, the lower deformation member 14 also moves upwards thereby exerting a greater pressure on the lower lateral surface of the specimen 17. In this regard, the pressure exerted by the lower deformation member 14 on the lower lateral surface is greater than the pressure exerted by the upper deformation member 15 on the upper lateral surface of the specimen 17. This results in the upward concave deflection of the specimen 17.

Apart from amplifying the bending amplitude directed to the specimen 17, the adjustment mechanism, which includes the amplifying lever 7 and the adjustable pivot 8, also allows the bending amplitude to be adjusted automatically by software instead of manually by hand. Also, the range of adjustment may be continuous and not just at discrete increments.

Figure 7:
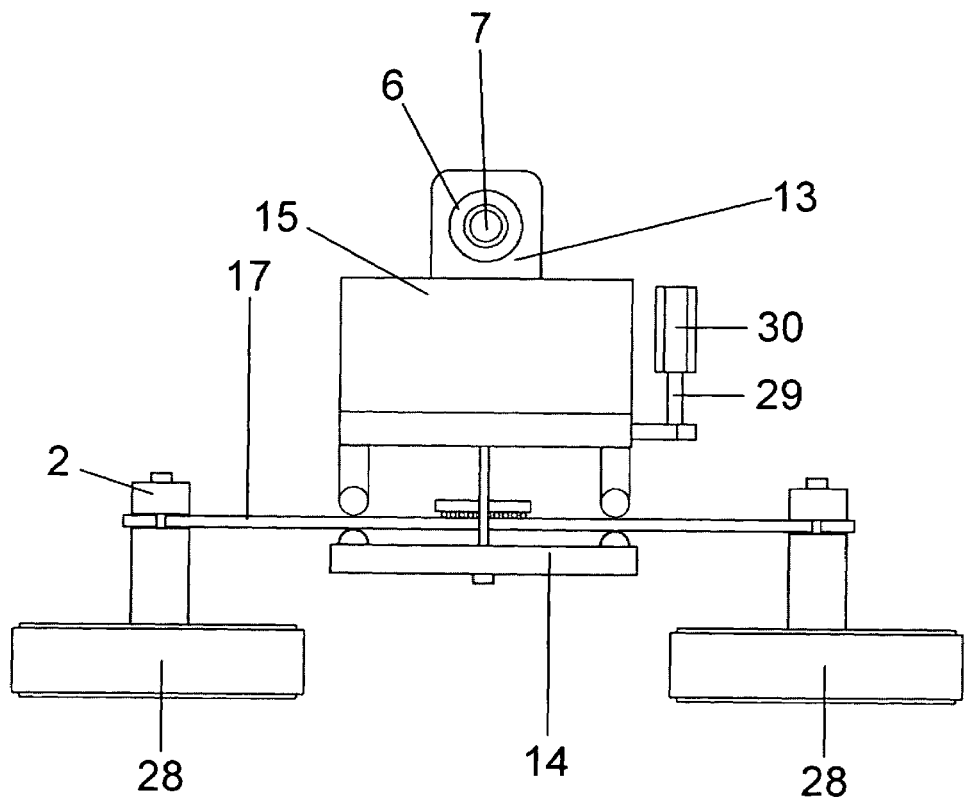
FIG. 7 shows a side view of an embodiment including a displacement transducer and load transducers.
Figure 8:
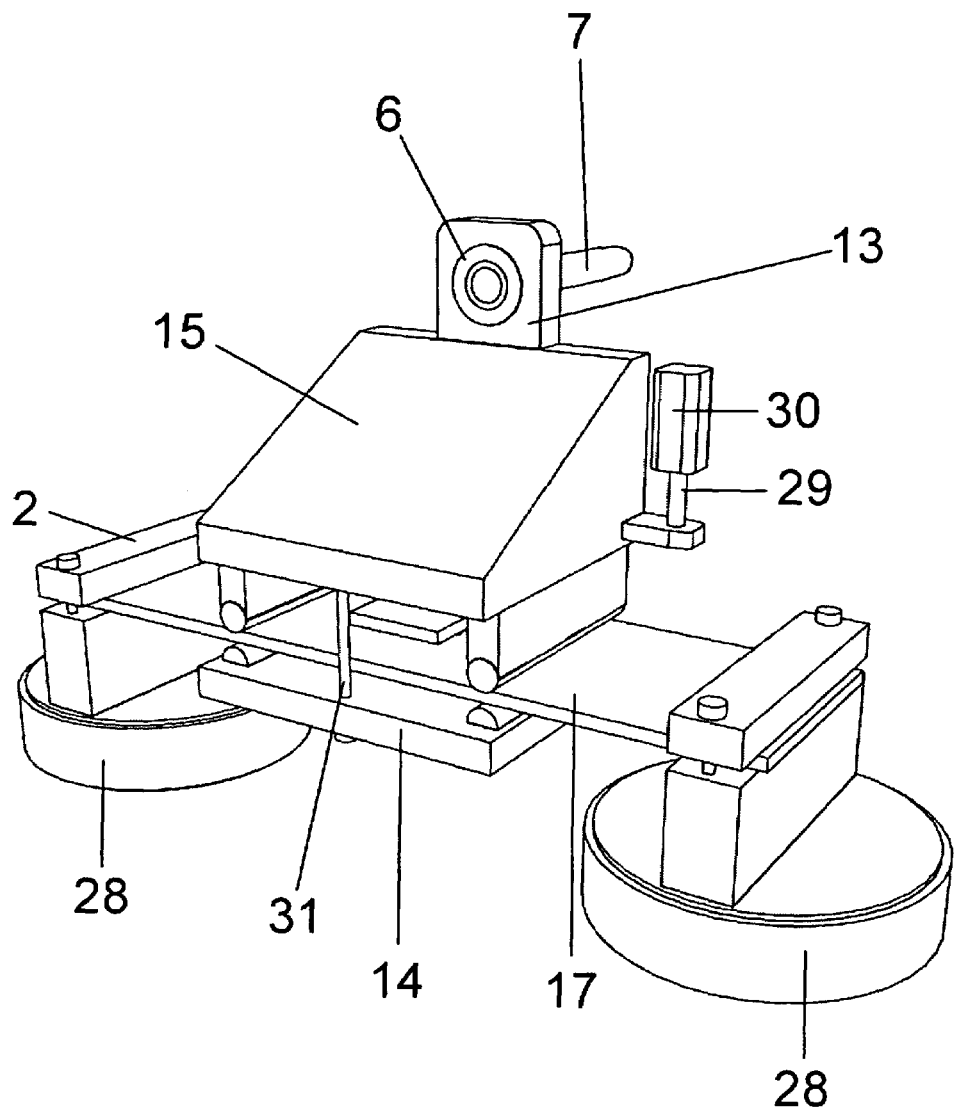
FIG. 8 shows an isometric view of the embodiment of the bend testing apparatus of FIG. 7.

FIG. 7 and FIG. 8 show a side view and a perspective view of a further embodiment according to the present invention. FIG. 7 shows deformation members 14 and 15, specimen holders 2, displacement transducer (which comprises a rod housing 30 and a push rod 29) and load transducers 28. The push rod 29 of the displacement transducer is connected to the upper deformation anvil 15 while the rod housing 30 is attached to a rigid reference frame (not shown). As the upper deformation member 15, which is connected to deformation member 14 through screw 31 (see FIG. 8), is deflected by lever 7, it moves push rod 29 which slides within sensor housing 30, thereby registering a displacement measurement. Specimen holders 2 are rigidly bolted to load cells 28 thereby allowing measurements of reaction forces at the supported ends of the test specimen 17.

Figure 9:
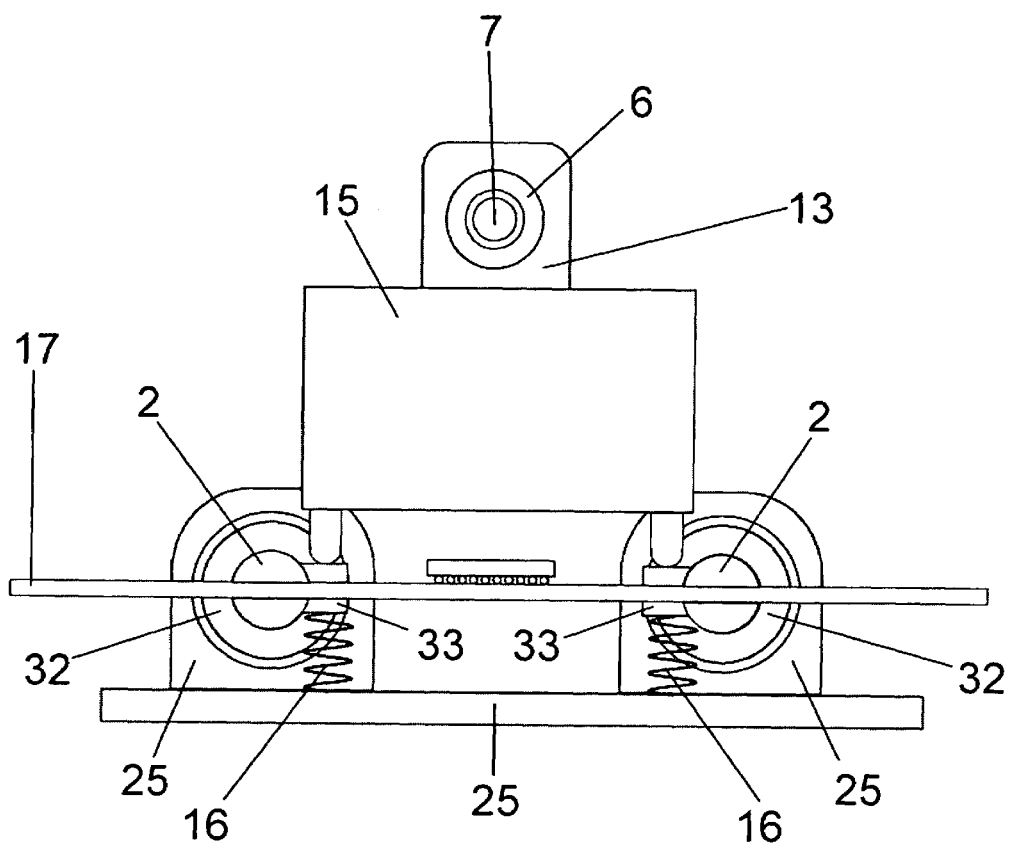
FIG. 9 shows a side view of an embodiment that allows both twisting and bending of a test specimen.
Figure 10A:
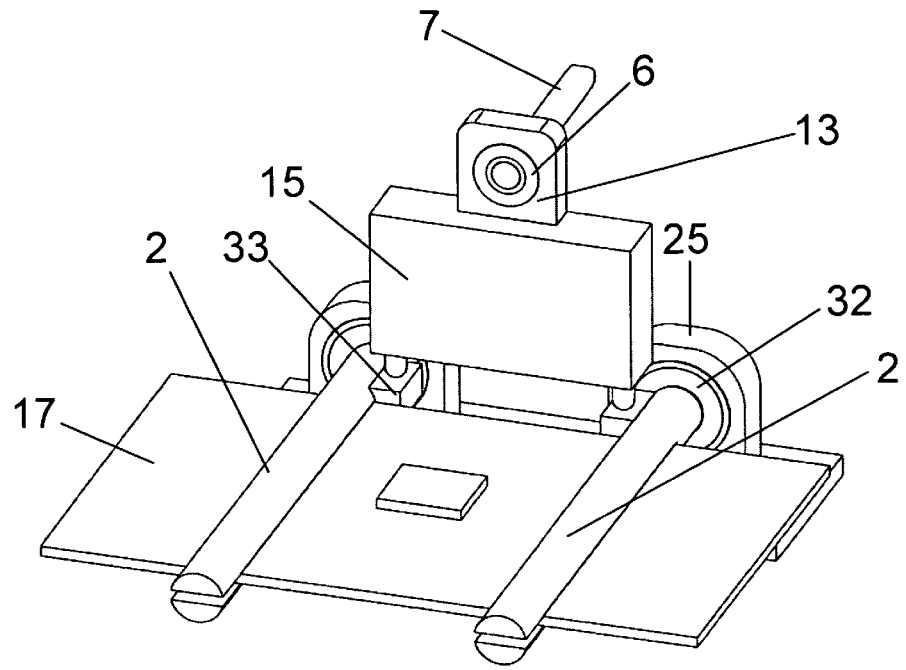
FIGS. 10A and 10B show perspective view of the embodiment of FIG. 9.
Figure 10B:
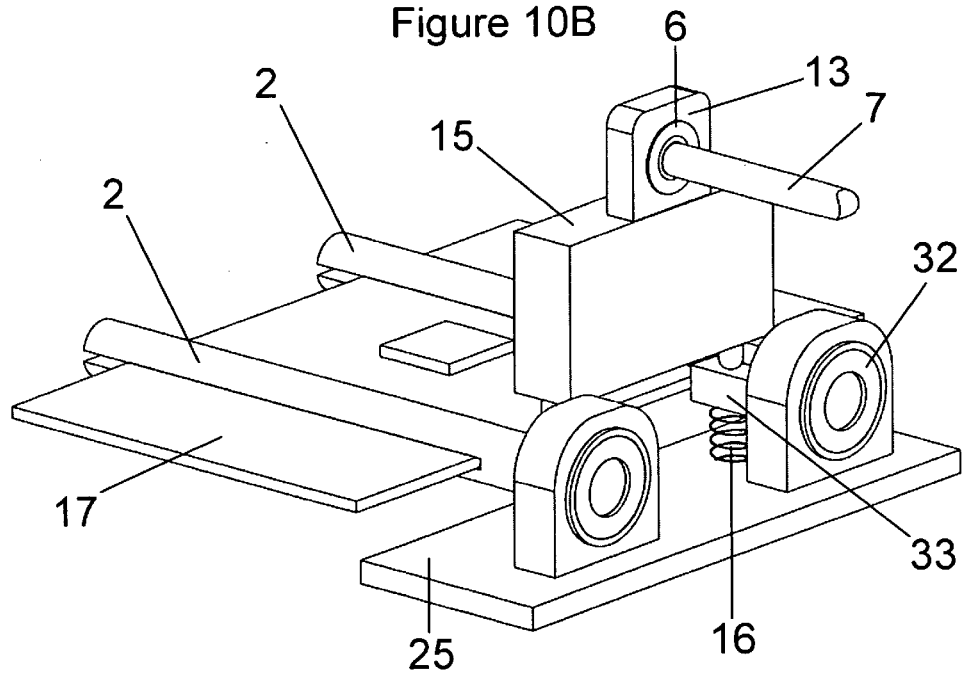

FIG. 9 and FIGS. 10A and 10B show a side view and perspective views of a further embodiment according to the present invention. This embodiment has only one deformation member 15 and a pair of specimen holders 2 that hold the test specimen in such a manner that it allows both twisting and bending of said test specimen 17. When the linear deflection applied by lever 7 causes deformation member 15 to push downwards, for example, against protrusions 33, which in turn are connected to specimen holders 2, there is a first angular rotation of the specimen holders 2 as they are mounted on rotational bearings 32. The specimen holder 2 rotate in opposing directions to each other, i.e. one specimen holder may rotate clockwise while the other rotates in a counter-clockwise (or anti-clockwise) manner. Accordingly, this results in a bending of the test specimen 17 such that the test specimen 17 is now flexed concave downwards. Conversely, on retraction of the deformation member 15 (i.e. the deformation member moves upwards), springs 16 rotate the specimen holders 2 in a direction opposite to their earlier rotation. Owing to the rotational nature of the load, the torsional stiffness of the specimen holders 2 may be adjusted to achieve both twisting and bending of the test specimen 17.

Figure 11A:
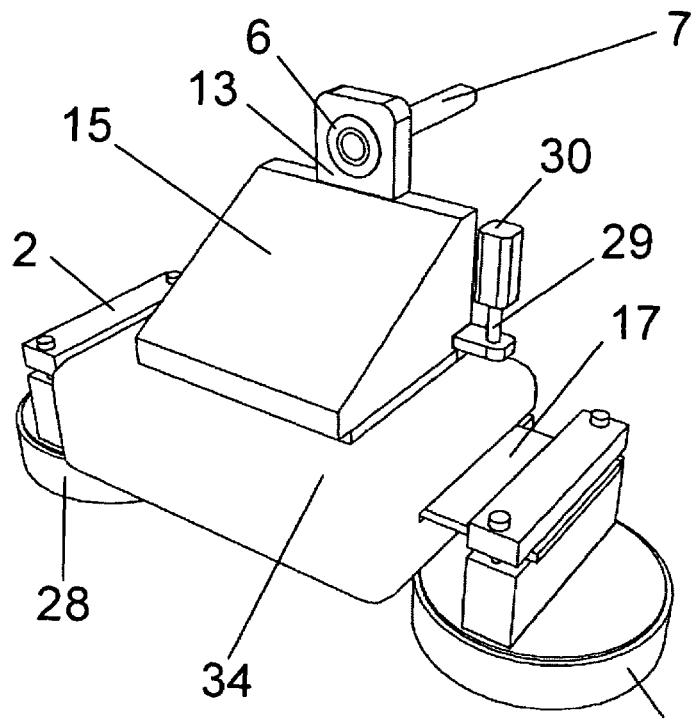
FIGS. 11A and 11B show a perspective view of an embodiment including a temperature chamber.
Figure 11B:
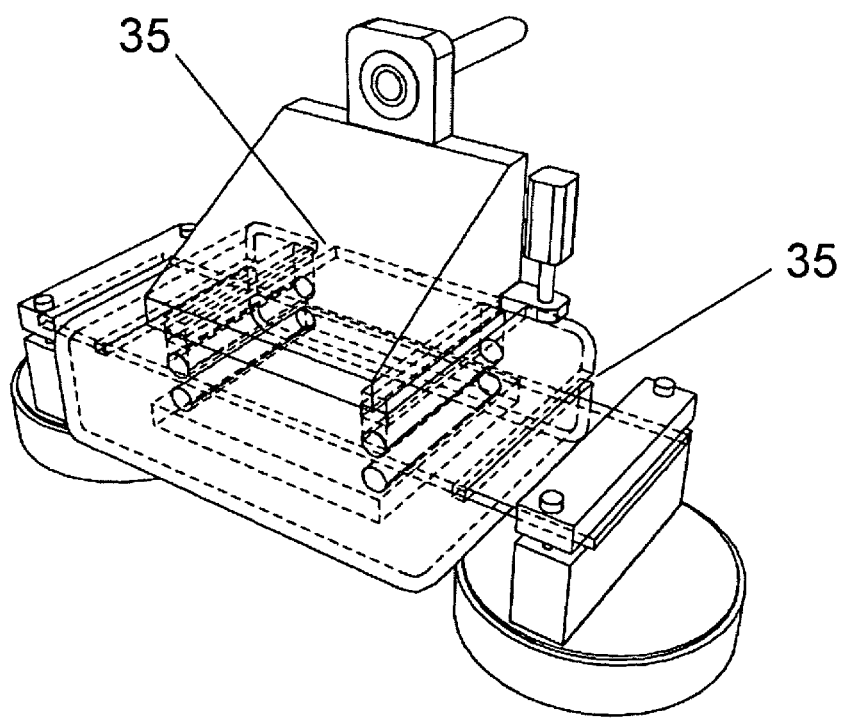

FIGS. 11A and 11B show perspective outline and hidden-line views of a further embodiment according to the invention. This embodiment is essentially the embodiment of FIGS. 9, 10A and 10B, and further includes a temperature chamber 34 that encloses test specimen 17. The temperature chamber 34 allows the bend testing to be conducted at low temperatures, for example. Alternatively, higher temperatures may also be used. The chamber walls of the temperature chamber 34 contain insulated openings 35 through which the deformation member 15 and specimen 17 pass through.

Figure 12:
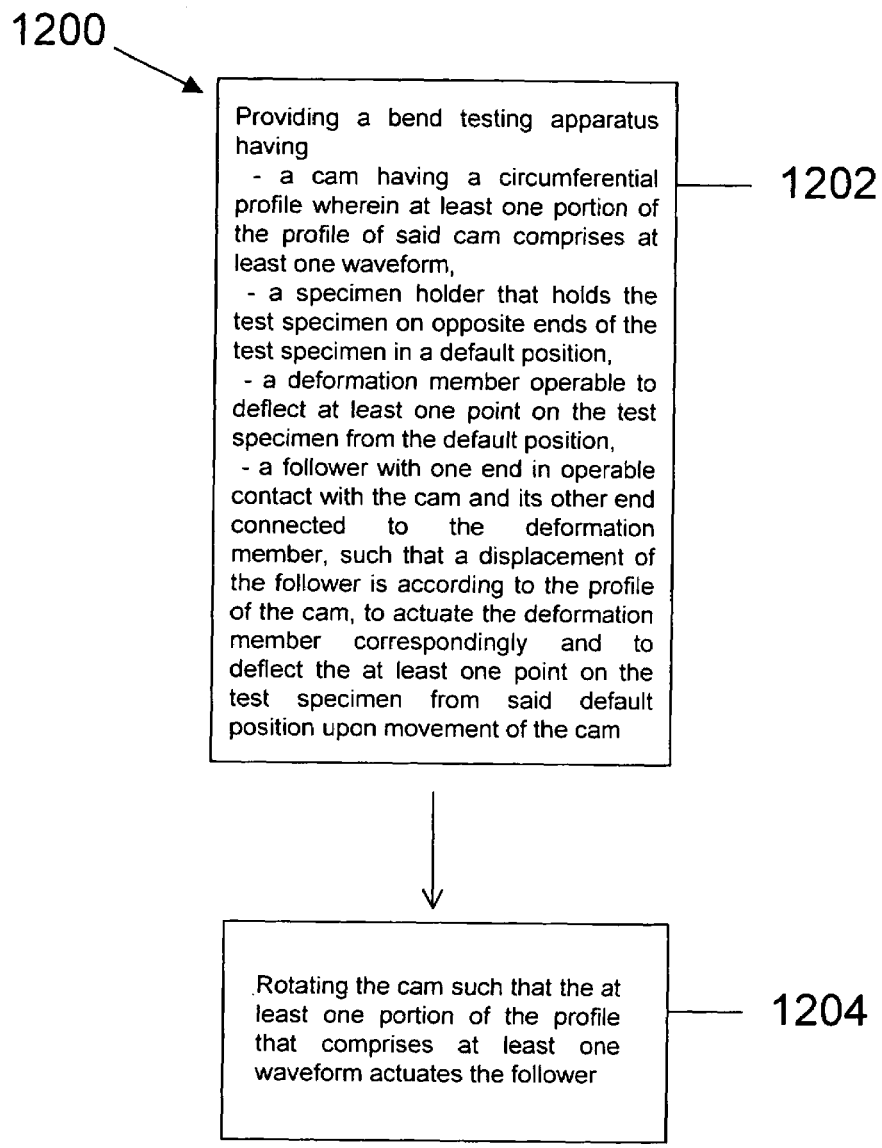
FIGS. 12 shows a flow diagram if a method for bend testing a test specimen at high speeds and frequencies.

FIG. 12 shows a flow diagram of a method 1200 for bend testing a test specimen at high speeds and frequencies. The method has two steps. The step 1202 is to provide a bend testing apparatus, said bend testing apparatus having a cam having a circumferential profile wherein at least one portion of the profile of said cam comprises at least one waveform The apparatus also includes a specimen holder that holds the test specimen on opposite ends of the test specimen in a default position, a deformation member operable to deflect at least one point on the test specimen from the default position and a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam. The step 1204 is to rotate the cam such that the at least one portion of the profile that comprises at least one waveform actuates the follower. Alternatively, any of the other exemplary embodiments bend testing apparatus of the invention, as described above, may of course also be used in the method.

The aforementioned description of the various embodiments has been presented for purposes of illustration and description. It is not intended to be exhaustive or to limit the invention to the precise form disclosed, and obviously many modifications and variations are possible in light of the disclosed teaching. It is intended that the scope of the invention be defined by the claims appended hereto.

What is claimed is:

1. A bend testing apparatus for simulating free vibrational flexing at high speeds and frequencies in a test specimen, said apparatus comprising:

a cam having a circumferential profile wherein at least one portion of the profile of said cam comprises at least one waveform, a specimen holder that holds the test specimen on opposite ends of the test specimen in a default position, a deformation member operable to deflect at least one point on the test specimen from the default position, and a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam.

2. The apparatus according to claim 1, wherein the cam is moveable linearly or rotationally.

3. The apparatus according to claim 2, further comprising a motor, wherein the motor is adapted to translate the cam linearly or rotationally.

4. The apparatus according to claim 3, wherein the rotationally translated cam or linearly translated cam further comprises a clutch adapted to engage said cam at a suitable motor speed.

5. The apparatus according to claim 4, wherein the rotationally translated cam is a disc.

6. The apparatus according to claim 4, wherein the linearly translated cam is a sliding platform.

7. The apparatus according to claim 5, further comprising a flywheel having a rotational centre, being arranged in-between the motor and the clutch such that the rotational centre rotates about the axis of rotation of the cam.

8. The apparatus according to claim 7, wherein the at least one waveform comprises a crest, a trough, a sinusoid or any combination thereof.

9. The apparatus according to claim 8, wherein the clutch is a fast response clutch.

10. The apparatus according to claim 9, wherein the fast response clutch comprises a wafer magnetic clutch, a reduced armature gap clutch or a magnetic particle clutch.

11. The apparatus according to claim 10, wherein the fast response clutch has a response time of less than about 60 milliseconds (ms).

12. The apparatus according to claim 11, wherein the cam and the deformation member are fabricated from a material selected from the group consisting of fiber-reinforced composites, polycarbonate, titanium, aluminum and composites thereof.

13. The apparatus according to claim 12, wherein the waveform has a rise angle that is between about ten to about sixty degrees.

14. A bend testing apparatus for simulating free vibrational flexing at high speeds and frequencies in a test specimen, said apparatus comprising:
a cam having a profile wherein said profile comprises at least one waveform on at least one circumferential portion of the cam,
a specimen holder that holds a test specimen on opposite ends of the test specimen in a default position,
a deformation member operable to deflect at least one point on the test specimen from the default position,
a follower with one end in operable contact with the cam and its other end connected to a lever, said lever being pivotally borne by a pivot at a position between the two ends thereof, to achieve an opposite movement of the one end of the lever and the deformation member connected thereto with respect to the movement of the other end of the lever operably connected with the follower, such that the displacement of the follower is according to the profile of the cam, thereby actuating the deformation member, via the pivotally borne lever, and to deflect the at least one point on the test specimen from said default position upon movement of the cam, and
an adjusting mechanism operably connected to the pivot, by which the position of the pivot can be adjusted along the axis of the lever.

15. The apparatus according to claim 14, wherein the rotationally translated cam further comprises a clutch adapted to engage said cam at its axis of rotation at a suitable motor speed.

16. The apparatus according to claim 15, further comprising a flywheel having a rotational centre, being arranged in-between the motor and the clutch such that the rotational centre rotates about the axis of rotation of the cam.

17. The apparatus according to claim 16, wherein the adjusting mechanism is controlled by a motor.

18. The apparatus according to claim 17, wherein the motor is controlled by a computer program element.

19. The apparatus according to claim 1, wherein the specimen holder is a bearing-mounted specimen holder that is rotatable and capable of converting a linear deflection of the test specimen into an angular rotation when said test specimen is linearly deflected by the deformation member.

20. The apparatus according to claim 19, wherein the bearing-mounted specimen holder is of an adjustable torsional stiffness.

21. The apparatus according to claim 1, further comprising a displacement transducer, said displacement transducer having a push rod slidably mounted within a housing where a free end of the push rod is connected to the deformation member and the housing is fixed to a rigid reference frame, such that a bending displacement of the test specimen results in a sliding displacement of the push rod with respect to the fixed housing.

22. The apparatus according to claim 1, further comprising load transducers rigidly supported and bolted to the specimen holders such that a force applied to the test specimen via the deformation member is measurable by said load transducers.

23. The apparatus according to claim 1, wherein the test specimen is enclosed by a compact temperature chamber comprising insulated openings for the deformation members and specimen to pass through and contact said test specimen.

24. The apparatus according to claim 14, wherein the specimen holder is a bearing-mounted specimen holder that is rotatable and capable of converting a linear deflection of the test specimen into an angular rotation when said test specimen is linearly deflected by the deformation member.

25. The apparatus according to claim 24, wherein the bearing-mounted specimen holder is of an adjustable torsional stiffness.

26. The apparatus according to claim 14, further comprising a displacement transducer, said displacement transducer having a push rod slidably mounted within a housing where a free end of the push rod is connected to the deformation member and the housing is fixed to a rigid reference frame, such that a bending displacement of the test specimen results in a sliding displacement of the push rod with respect to the fixed housing.

27. The apparatus according to claim 14, further comprising load transducers rigidly supported and bolted to the specimen holders such that a force applied to the test specimen via the deformation member is measurable by said load transducers.

28. The apparatus according to claim 14, wherein the test specimen is enclosed by a compact temperature chamber comprising insulated openings for the deformation members and specimen to pass through and contact said test specimen.

29. A method of bend testing a test specimen at high speeds and frequencies, said method comprising
providing a bend testing apparatus comprising:
a cam having a circumferential profile wherein at least one portion of the profile of said cam comprises at least one wave form,
a specimen holder that holds the test specimen on opposite ends of the test specimen in a default position,
a deformation member operable to deflect at least one point on the test specimen from the default position,
a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam; and Rotating the cam such that the at least one portion of the profile that comprises at least one waveform actuates the follower.

30. The method according to claim 29, wherein the test specimen is a printed circuit board (PCB).

31. A bend testing apparatus for simulating free vibrational flexing at high speeds and frequencies in a test specimen, said apparatus comprising:
  a disc that is moveable linearly or rotationally having a circumferential profile wherein at least one portion of the profile of said disc comprises at least one waveform comprising a crest, a trough, a sinusoid or any combination thereof;
  a motor adapted to translate the disc linearly or rotationally wherein the motor comprises a fast response clutch adapted to engage the disc at a suitable motor speed;
  a specimen holder that holds the test specimen on opposite ends of the test specimen in a default position;
  a deformation member operable to deflect at least one point on the test specimen from the default position;
  a follower with one end in operable contact with the disc and its other end connected to the deformation member, such that a displacement of the follower is according to the profile of the disc, to actuate the deformation member correspondingly and to deflect the at least one point on the test specimen from said default position upon movement of the disc; and
  a flywheel having a rotational centre, being arranged in-between the motor and the clutch such that the rotational centre rotates about the axis of rotation of the disc.

32. The apparatus according to claim 31, wherein the fast response clutch has a response time of less than about 60 milliseconds (ms).

33. The apparatus according to claim 32, wherein the disc and the deformation member are fabricated from a material selected from the group consisting of fiber-reinforced composites, polycarbonate, titanium, aluminum and composites thereof.

34. A bend testing apparatus for simulating free vibrational flexing at high speeds and frequencies in a test specimen, said apparatus comprising:
  a cam having a circumferential profile wherein at least one portion of the profile of said cam comprises at least one waveform,
  a specimen holder that holds the test specimen on opposite ends of the test specimen in a default position,
  a deformation member operable to exert a force on the upper and lower surfaces of the test specimen to deflect at least one point on the test specimen in an upward or downward deflection away from the default position, and
  a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam.

35. A method of bend testing a test specimen at high speeds and frequencies, said method comprising
  Providing a bend testing apparatus comprising:
    a cam having a circumferential profile wherein at least one portion of the profile of said cam comprises at least one wave form,
    a specimen holder that holds the test specimen on opposite ends of the test specimen in a default position,
    a deformation member operable to exert a force on the upper and lower surfaces of the test specimen to deflect at least one point on the test specimen in an upward or downward deflection away from the default position,
    a follower with one end in operable contact with the cam and its other end connected to the deformation member, such that a displacement of the follower is according to the profile of the cam, to actuate the deformation member correspondingly and to deflect the at least one point on the test specimen from said default position upon movement of the cam; and
  rotating the cam such that the at least one portion of the profile that comprises at least one waveform actuates the follower.

* * * * *

UNITED STATES PATENT AND TRADEMARK OFFICE
CERTIFICATE OF CORRECTION

PATENT NO.       : 7,464,606 B2                                          Page 1 of 1
APPLICATION NO.  : 11/406546
DATED            : December 16, 2008
INVENTOR(S)      : Ee Hua Wong, Kah Woon Simon Seah and Ranjan s/o Rajoo It is certified that error appears in the above-identified patent and that said Letters Patent is hereby corrected as shown below:

On the Title page, Item 75

Inventors:  Insert --Simon-- between Woon Seah of second listed inventor

On the Title page, Item 73

Assignee:  Insert --National University of Singapore-- as second listed assignee Signed and Sealed this Thirty-first Day of March, 2009

JOHN DOLL
*Acting Director of the United States Patent and Trademark Office*